United States Patent [19]

Klein et al.

[11] Patent Number: 5,093,118

[45] Date of Patent: Mar. 3, 1992

[54] **ANTIGEN OF *BLASTOMYCES DERMATITIDIS* AND ITS USES**

[75] Inventors: Bruce S. Klein; Jeffrey M. Jones, both of Madison, Wis.

[73] Assignee: Wisconsin Alumni Research Foundation, Madison, Wis.

[21] Appl. No.: 406,999

[22] Filed: Sep. 14, 1989

[51] Int. Cl.$^5$ ................. G01N 33/532; C07K 15/10
[52] U.S. Cl. ........................ 424/88; 530/371; 530/806; 530/824; 435/7.24; 436/544
[58] Field of Search ............... 530/371, 806, 824; 424/88

[56] References Cited

U.S. PATENT DOCUMENTS

| | | | |
|---|---|---|---|
| 3,887,431 | 6/1975 | Robbins et al. | 530/371 |
| 4,080,260 | 3/1978 | Chao | 530/371 |
| 4,123,427 | 10/1978 | Daniel | 530/370 |

OTHER PUBLICATIONS

Green et al, "Preparation of Reference Antisera for Laboratory Diagnosis of Blastomycosis", *J. Clin. Microbiol.*, vol. 10, No. 1, Jul. 1979, pp. 1–7.
Klein et al, "Isolation, Purification, and Radiolabelling of a Novel 120-KD Surface Protein . . . ", *J. Clin. Invest.*, vol. 85, Jan. 1990, pp. 152–161.
Moyers, "The Isolation and Characterization of Soluble Yeast Phase Antigens of Blastomyces Dermatitidis", *Diss. Abstr. Int. B.* 1979, 40(3), 1066.
L. Kaufman et al., 26 Appl. Microbiol., 244–247 (1973).
R. Cox et al., 10 Infec. Immun. 42–47 (1974).
R. Cox et al., 10 Infec. Immun., 48–53 (1974).
M. Lancaster, 13 Infec. Immun., 758–762 (1976).
F. Deighton et al., 15 Infec. Immun., 429–435 (1977).
J. Green et al., 4 Curr. Microbiol., 293–296 (1980).
K. Young et al., 33 Infec. Immun., 171–177 (1981).
R. Bradsher et al., 33 Infec. Immun., 485–490 (1981).
R. Bradsher, 129 Am. Rev. Respir. Dis., 430–434 (1984).
S. Turner et al., 23 J. Clin. Microbiol., 294–297 (1986).
J. Jones, 30 Infec. Immun., 78–89 (1980).
R. Greenfield, 101 J. Lab. Clin. Med., 758–771 (1983).
B. Klein et al., 314 N. Engl. J. Med., 529–534 (1986).
B. Klein et al., 133 Am. Rev. Respir. Dis., 144–148 (1986).
B. Klein et al., 155 J. Infec. Dis., 262–268 (1987).
B. Klein et al., 136 Am. Rev. Respir. Dis., 1333–1338 (1987).
F. Kanetsuna et al., 97 J. Bacteriol., 1036–1041 (1969).
F. Kanetsuna et al., 106 J. Bacteriol., 946–948 (1971).
K. Lee et al., 13 Sabouraudia, 148–153 (1975).
E. Reiss, Molecular Immunology of Mycotic and Actinomycotic Infections, 77–102, Elsevier/N.Y. (1986).
U. Laemmli, 227 Nature, 680–685 (1970).
J. Heukeshoven et al., 6 Electrophoresis, 103–112 (1985).
R. Kapitany et al., 56 Anal. Biochem., 361–369 (1973).
H. Towbin et al., 76 P.N.A.S., USA, 4350–4354 (1979).
P. Minden et al., Handbook of Experimental Immunology, F. A. Davis Co., 463–492 (1967).

*Primary Examiner*—Jeffrey E. Russel
*Attorney, Agent, or Firm*—Quarles & Brady

[57] ABSTRACT

A cell wall protein of the fungus *B. dermatitidis* is isolated and purified. The protein is readily recognized by serum antibodies from animals having blastomycosis. The protein antigen can be labelled to provide an assay for detection of the disease, it can be used to stimulate specific lymphocyte response and thereby provide another assay for detection of the disease, it can be used to produce an immune response to *B. dermatitidis*, or it can be used to create antibodies to the protein.

4 Claims, No Drawings

ANTIGEN OF *BLASTOMYCES DERMATITIDIS* AND ITS USES

This invention relates to a protein that is present on the yeast form of the fungus *Blastomyces dermatitidis*. More particularly, it relates to the isolation and purification of the protein, to the use of the protein to test for the past or present presence of a disease caused by the yeast, and to the use of the protein to produce an immune response against the *B. dermatitidis* from an animal.

BACKGROUND OF THE INVENTION

Blastomycosis is a disease caused by infection with the fungus *Blastomyces dermatitidis.* Humans and other animals (particularly dogs) are infected by inhaling aerosolized fungal spores from soil where the organism dwells. At body temperature, these spores convert to yeast forms. Acute primary pulmonary infection caused by the yeast can produce an influenza or pneumonia syndrome Although acute blastomycotic pneumonia may resolve spontaneously, progressive forms of disease can cause serious damage to the lungs, skin, bones, joints, or prostate gland.

Although serologic and skin tests play an important role in the identification and epidemiologic study of other mycoses, reliable markers of recent and remote *B. dermatitidis* infection are not generally available for non-invasive diagnosis and study of the epidemiologic features of blastomycosis. The best available tests involve two antigens taken from *B. dermatitidis* yeast, "A" antigen (see J. Green et al., 4 Curr. Microbiol. 293–96 (1980)) and "Blastomyces alkali- and water-soluble antigen (B-ASWS)" (see R. Cox et al., 10 Infect Immun. 42–47 (1974)). These two prior art antigens are impure (see K. Young et al., 33 Infect Immun. 171–177 (1981); M. Lancaster et al., 13 Infect Immun 758–762 (1976)), they appear to be a mixture of cell wall components, and tests employing them are not widely available A further problem with serologic tests using, for example, the "A" antigen has been diminished specificity as sensitivity is increased. This problem appears to result from antigen impurity and the extensive sharing of cell wall components between dimorphic fungi, particularly *B. dermatitidis* and *Histoplasma capsulatum.*

It is also desirable to develop a vaccine for the disease. In this regard, approximately fifteen percent of infected humans and over two-thirds of infected dogs die when infected with this fungus.

Thus, it can be seen that a need exists for the development of a test for the presence of *B. dermatitidis* in an animal which has high sensitivity, high specificity, and which can easily and quickly be performed at low cost. Vaccines against the disease are also needed.

SUMMARY OF THE INVENTION

One embodiment of the present invention provides an assay for the presence in a sample of antibody to *Blastomyces dermatitidis.* One exposes the sample to a labelled proteinaceous material which the antibody will bind to and then measures the degree of binding of the antibody to the labelled proteinaceous material. In accordance with the present invention, the material is WI-1 proteinaceous material. In a preferred form, this is done by precipitating out antigen bound to antibody. The proteinaceous material can be obtained from *Blastomyces dermatitidis* by freezing the yeast In the alternative, the material can be synthetically created or the gene for the protein can be located, cloned, and expressed.

The proteinaceous material preferably either contains the whole WI-1 protein or contains a portion of WI-1 protein which is between 110,000 and 125,000 in molecular size, the label can be a radioactive label, and the assay can be developed with cut off levels and controls such that it can distinguish antibody to *B. dermatitidis* from antibody to *Histoplasma capsulatum.*

In another embodiment of the invention, the WI-1 proteinaceous material itself is provided. It can be obtained by obtaining an extract of *Blastomyces dermatitidis* after freezing the yeast. Preferably, the material contains no *B. dermatitidis* protein except for WI-1. In yet another form, the material can be used to produce an immune response to *B. dermatitidis* by an animal by providing it to an animal with a suitable carrier (typically a liquid), and/or to create hybridomas and antibodies.

In yet another form, there is provided an assay to determine the propensity of lymphocytes to proliferate in the presence of proteinaceous material from *Blastomyces dermatitidis.* One exposes the lymphocytes to WI-1 proteinaceous material and then measures the amount of resulting proliferation of the lymphocytes. The exposing step can take place in the presence of labelled nucleosides or labelled nucleotides. The more labelled nucleotide/nucleoside that is incorporated during the exposing step, the more the lymphocyte has previously been exposed to the fungus.

It will be appreciated that the inventors have located and isolated a cell wall protein of *B. dermatitidis* which is present in sufficient amounts in infected animals that specific antibodies to this protein are readily detectable in these animals. The protein does not appear to be present with other fungal diseases By labelling the protein and then using the protein as an antigen to test for antibodies in animal serum, one can test for the presence of the disease. The protein antigen (called "WI-1") can easily be labelled with radioactive iodine or other labels. To test for remote past infection with the disease, lymphocytes are tested for their "memory" of the disease by exposing them to the protein and monitoring proliferation rates. The unlabelled antigen can also produce an immune response to *B. dermatitidis* if injected into animals.

The objects of the invention therefore include:

(a) providing WI-1 in substantially pure form;

(b) providing an assay for antibodies to *B. dermatitidis* that uses labelled WI-1 as an antigen;

(c) providing a highly specific, sensitive and low cost diagnostic test for *B. dermatitidis;*

(d) providing a test for remote past infection by *B. dermatitidis;*

(e) providing a vaccine to inhibit infection by *B. dermatitidis;* and (f) providing antibodies to WI-1.

These and still other objects and advantages of the present invention will be apparent from the description which follows. These embodiments do not represent the full scope of the invention. Rather, the invention may be employed in other embodiments. Reference is therefore made to the claims herein for interpreting the scope of the present invention.

BEST MODES FOR CARRYING OUT THE INVENTION
General Overview

An extract of *B. dermatitidis* yeast is prepared by freezing the yeast in a dilute buffer, separating the supernatant from organism by centrifugation, dialyzing the supernatant against distilled water, and lyophilizing the salt free supernatant (the "freeze extract"). The antigen, WI-1, is identified in the freeze extract by its migration in a sodium dodecyl sulfate-polyacrylamide gel (SDS-PAGE). It migrates to a location near a 118 kDa molecular size marker, indicating that WI-1 has a molecular size of between 110,000 to 125,000. WI-1 is further identified by its recognition by antibodies in a panel of sera from patients with documented blastomycosis, and its failure to be recognized by antibodies in sera from patients with documented histoplasmosis, sporotrichosis, coccidioidomycosis, or candidiasis.

The WI-1 antigen can be purified by electroelution from SDS-PAGE gels loaded with the freeze extract and by ion exchange chromatography using high pressure liquid chromatography (HPCL) techniques. A preparative HPLC column (such as a TSK DEAE 5-PW) can be loaded with freeze extract which has been dissolved in 25 mM tris(hydroxymethyl)aminomethane buffer (pH 7.78). A binary gradient system is used with increasing concentrations of NaCl being pumped through the column. WI-1 elutes from the column when the NaCl concentration reaches 460–490mM. The purified WI-1 gives a single band when analyzed using a SDS-PAGE gel. The extract therefore is essentially free of other *B. dermatitidis*-derived cell wall proteinaceous material of under 110 kD or over 125 kD.

WI-1 can be used in immunoassays designed to demonstrate presence of anti-WI-1 antibodies or lymphocytes reactive with WI-1. This use of the antigen has been shown in a radioimmunoassay, which can detect anti-WI-1 in human sera. With the radioimmunoassay, it has been demonstrated that WI-1 does not react with human antibodies against *Histoplasma capsulatum* (or for that matter *Coccidioides immitis, Sporothrix schenckii,* or *Candida albicans*). ELISA and other forms of immunoassay can also be developed based on using the antigen. Also, antibodies to WI-1 were demonstrated in sera from rabbits immunized with purified WI-1.

Specific stimulation of human lymphocytes by WI-1 has been demonstrated with a standard blast transformation assay using lymphocytes from humans infected with Blastomyces. Further, it has been shown that WI-1 can be used to immunize animals. This has been exemplified by immunizing rabbits with WI-1 incorporated into Freund's adjuvant and detecting anti-WI-1 antibodies in sera from the immunized rabbits.

Obtaining WI-1 A Fungi.

Five American Type Culture Collection (ATCC) strains of *B. dermatitidis* were studied 60636, 60637, 26198, 32090, and 26199. Stock cultures were maintained in the yeast form on 7H10 agar enriched with oleic acidalbumin complex (Sigma Chemical Co., St. Louis, Mo.) at 37° C. Yeasts were grown in Erlenmeyer flasks containing brain heart infusion (BHI) broth (Difco Laboratories, Detroit, Mich.) at 37° C. in a gyrator shaker at 120 rpm for 72 hours. All yeasts were harvested by filtration through a sintered glass filter and washed three times with saline. Freshly grown yeasts were used in experiments unless otherwise stated, in which case yeasts that had been stored at −20° C. in 20 mM Tris-HCL, pH 6.8, containing 1 mM $MgCl_2$ were used.

For comparison experiments, *B. dermatitidis* A antigen (kindly provided by Dr. Leo Kaufman, Centers For Disease Control Atlanta, Ga.) and B-ASWS (kindly provided by Dr. Rebecca Cox, San Antonio Chest Hospital, San Antonio, Tex.) were used.

B. Extraction Of *B. dermatitidis*

Yeasts that had been stored at −20° C. were thawed and centrifuged at 600×g for 10 minutes. The supernatant, which we termed the freeze extract, was then removed and dialyzed for 48 hours against deionized-distilled water in nitrogen-purged dialysis tubing with a 3,500-molecular weight exclusion. Dialysates were lyophilized to obtain dry extracts.

C. Sodium dodecyl sulfate—polyacrylamide gel electrophoresis (SDS-PAGE)

A portion of the extract was prepared for SDS-PAGE analysis by dissolving an extract at a concentration of 40 mg (dry wt)/ml in sample buffer containing 0.125 M Tris-HCL, 4% (wt/vol) SDS, 2% (wt/vol) glycerol, and 10% (vol/vol) 2-mercaptoethanol (pH 6.8). After boiling for 2 minutes, samples were electrophoresed on 10% SDS-PAGE slab gels as described by U. Laemmli, 227 Nature 680–685 (1970). Gels were stained for protein with Coomassie brilliant blue or silver nitrate J. Heukeshoven et al., 6 Electrophoresis 103–112 (1985) and for carbohydrate by the periodic acid-Schiff (PAS) method of R. Kapitany et al., 56 Anal. Biochem. 361–369 (1973).

D. Western blots

Upon completion of SDS-PAGE, Western blots of gels were prepared as described by H. Towbin et al., 76 P.N.A.S. USA 4350–4354 (1979). Nitrocellulose paper was placed on the gel in a cassette in a Transphor electrophoresis chamber (Hoeffer Scientific Instruments, San Francisco, Calif.) filled with 20 mM tri base containing 150 mM glycine and 20% (vol/vol) methanol. Gel components were transferred to the nitrocellulose paper by passing a current transversely across the cassette for 18 hours at 70 V.

The nitrocellulose was placed in a solution of 3% BSA in tris buffered saline (TBS) (BSA-TBS; 50 mM Tris-HCL, 200 mM NaCl [pH 7.4]) at 40° C to saturate unoccupied sites on the paper with albumin. The paper was cut vertically into strips and a strip was incubated for 2 hours at room temperature with the desired serum diluted 1:10 in TBS. Strips were washed in six changes of saline (5 minutes each) and exposed to the appropriate conjugate, either peroxidase-conjugated sheep anti-rabbit IgG or peroxidase-conjugated rabbit anti-human IgG (Cooper Biomedical, Inc., West Chester, Penna.). Conjugates were diluted 1:2,000 in saline containing 3% (wt/vol) BSA and 10% (vol/vol) fetal calf serum. Nitrocellulose strips were again washed in saline and developed for 30 minutes with a substrate solution (0.05% [wt/vol] 4-chloro-1-naphtol [Sigma], 0.015% [vol/vol] $H_2O_2$ in TBS). The above technique was modified slightly for miniblots. After unoccupied sites on the nitrocellulose were saturated with albumin, the uncut paper was placed into a 48-lane miniblotting apparatus (Immunetics, Boston, Mass.).

Reagents and steps otherwise the same as above. Western blots were made from 10% SDS-PAGE gels loaded with 25 mg of the cell wall extract.

Sera from patients with blastomycosis or histoplasmosis or from healthy persons were used to develop the blots to identify immunoreactive molecules in the cell wall recognized only by the first group. A 120 kD protein in the freeze extract was recognized by all ten patients with blastomycosis, but by none of the five with histoplasmosis and none of the four healthy persons. Western blots using thirty-three sera from an additional 25 patients with blastomycosis and both postimmunization sera from two immunized rabbits consistently showed staining of the 120 kD molecule, whereas preimmunization sera from the rabbits did not.

E. Purification of protein antiqen

An electrophoretic concentrator (ISCO, Inc., Lincoln, Nebr.) was then used to elute and concentrate WI-1 from the remaining crude freeze extracts. After the remaining extract was separated on a 10% SDS-PAGE gel, the location of WI-1 was estimated from the above knowledge of its molecular weight and the location in the gel of prestained molecular weight markers. A 0.5 cm horizontal strip was cut from the unstained gel corresponding to the 118 kD molecular weight marker, $\beta$-galactosidase. The gel strip was cut into pieces and placed in a transparent polycarbonate sample cup having a small and a large well that contained a 1:10 dilution of 25 mM Tris-base, pH 8.3, and 192 mM glycine. The cup in turn was bathed in a buffer tank containing the undiluted buffer. Three watts were applied across the buffer tank for 4 hours to elute WI-1 from the gel and concentrate it in 250 $\mu$l of buffer in the small well, whose base was covered with a membrane having a 3,500-molecular weight exclusion. This eluate was further concentrated by centrifugation at 5,000×for 30 minutes in a Centricon ® tube (Amicon Corp., Danvers, Mass.). The purity of the eluate was assessed by SDS-PAGE, and the protein content by using the Pierce Reagant (Pierce).

In the preferred form, strain 60636 was used in these experiments. Forty milligrams of the crude extract derived by freezing and thawing the organism was loaded onto a 10% gel along with a prestained molecular weight marker. The buffer front was run past the anode for approximately 90 minutes to separate the approximately 120 kD molecule from other extract components that resolved nearby. A 0.5 cm strip cut from the gel at the estimated region of this molecule thereby gave a purer protein fraction that would otherwise be possible. When analyzed by SDS-PAGE, the protein eluted from such gel strips generally yielded a single band when stained with Coomassie blue. The band could not be visualized with PAS stain. Eluates obtained from multiple electroelutions were pooled and concentrated. The final protein concentration of this material was 4 mg/ml.

Densitometry readings of the crude freeze extract showed that the molecule of interest resolved at 220±5 kD in strain 60636, however, slight variability in expression and size was noted among the five ATCC strains studied. Integration of the densitometry readings showed that the 120 kD molecule comprised 5% of the total protein present in the crude freeze extract of strain 60636.

Boiling the crude extract at 100° C. for 15 minutes or storing it at −20° C. either as a lyophilized powder or dissolved in treatment buffer did not appreciably alter the integrity of the 120 kD molecule as judged by SDS-PAGE. However, when several large batches of freeze extract were concentrated at 40° C. using a YM 100 filter (Amicon Corp.) prior to dialysis and lyophilization, the intensity of the band corresponding to WI-1 on SDS-PAGE gels loaded with the resultant material was diminished and the apparent molecular weight of WI-1 decreased to as low as 115 kD.

Electron microscopy and IFA and immunogold staining confirmed a cell wall location for the 120 kD molecule. Freezing apparently roughens the cell wall surface morphologically but does not appear to compromise its integrity, suggesting that the 120 kD molecule and other components in this crude extract represent superficial cell wall determinants. Consistent with this hypothesis, serum from a rabbit immunized with the 120 kD molecule stained the surface of *B. dermatitidis* yeasts in IFA and immunogold tests, whereas preimmune serum from this animal and the PBS control did not.

RIA Assay Techniques

A total of 267 sera from 185 patients and control subjects were tested by a radioimmunoassay for antibody to WI-1. Using this assay, an antibody titer of 1:40 or greater was detected in 58 (85%) of the 68 patients with blastomycosis, but in only 2 (3%) of the 73 patients previously believed to have only other mycoses and in none of the 44 healthy persons.

The basic idea of the preferred RIA is to label WI-1 with radioactive iodine, mix the labelled WI-1 with the serum, add a precipitating compound (e.g. Staphylococcal Protein A) that will cause protein bound to antibody to precipitate out, separate the precipitated material from the liquid, measure the radioactivity of either the precipitate or the liquid, and compare the results to controls. WI-1 can be labelled with $^{125}$I using N-chlorobenzenesulfonamide as an oxidizing agent. See J. Jones, 30 Infect. Immun. 78–89 (1980). By adjusting labelling conditions, we could vary the specific radioactivity of [$^{125}$I] WI-1 between 2,000 and 10,000 cpm/ng. When labelled to a specific radioactivity of 2,000 cpm/ng, the capacity of [$^{125}$I] WI-1 to bind specific antibody was stable for at least one month. Counting efficiency of the gamma counter was 60%.

We used 1% BSA in 0.04 M NaH$_2$PO$_4$, 0.15 M NaCl, pH 7.5 (PBS) as the carrier solution in the RIA. All sera being tested were diluted serially in BSA-PBS in flat-bottom, 96-well microtiter plates (Costar, Cambridge, Mass.). Dilutions of 1:40 and greater were tested. Each experimental or control serum sample was analyzed in duplicate. A test sample consisted of 0.1 ml of diluted serum and 0.1 ml of BSA-PBS containing 5 ng of [$^{125}$I] WI-1. Coprecipitation controls for antibody measurements contained 0.1 ml of BSA-PBS in place of diluted test serum. After incubating for 1 hour at 37° C. and overnight at 4° C., 1 mg of the Staphylococcal Protein A (Sigma) in 0.2 ml of PBS was added to each sample. Precipitates were centrifuged at 2,000×g or 10 minutes at room temperature and 0.2 ml of each supernatant was counted in a gamma counter.

Coprecipitation was corrected for in all RIAs by the method of P. Minden et al., Handbook Of Experimental Immunology 463–492 (1967). Coprecipitation never exceeded 10% of labelled antigen added and was usually under 5%. The dilution of each latest serum that specifically bound 20% of the labelled antigen dose was calculated by linear regression analysis (J. Jones, 30 Infect. Immun. 78–89 (1980)), using the data points of the three dilutions that have binding values closest to 20%. A standard lot or rabbit antiserum derived by immunizing the animal with unlabelled WI-1 was assayed with each run of experimental sera titered for antibody to the labelled antigen. This insured that there was no significant run-to-run variation in the sensitivity of the assay.

The RIA was used to quantitate the amount of WI-1 on the surface of *B. dermatitidis* (strain 60636), *H. capsulatum* and *C. albicans* yeasts. The specific inhibition of binding of [$^{125}$I] WI-1 to diluted rabbit antiserum was measured for unlabelled WI-1 and these yeasts. Each assay tube contained 0.1 ml of rabbit antiserum diluted in a carrier solution (1:80, vol/vol, 1% BSA-PBS) so as to bind approximately 60% of 5 ng of [$^{125}$I] WI-1. Inhibitor (either unlabelled antigen or yeasts in 0.1 ml of BSA-PBS) was added to each tube and the tubes were incubated at 37° C. for 1 hour and 4° C. for 4 hours. Then, [$^{125}$I] WI-1 (5 ng in 0.1 ml of BSA-PBS) was added to each tube and the tubes were incubated at 37° C. for 1 hour and at 4° C. overnight. The amount of [$^{125}$I] WI-1 specifically bound to antibody was determined for each tube. To generate a standard inhibition curve, solutions with known quantities of unlabelled antigen (0.25 to 500 ng in 0.1 ml) were used as inhibitors.

Various other assays can be designed based on WI-1. For example, WI-1 can be bound to a well (the well then being the "label"). Serum can then be washed over the well and various known anti-antibody systems can be used to identify the level of WI-1 antibody bound to the wells. ELISA or other techniques can also be used.

Lymphocyte Assay

Standard microtiter methods were adapted for a WI-1 lymphocyte proliferation assay. See generally R. Bradsher et al., 33 Infect. Immun. 485–490 (1981); R. Bradsher, 129 Am. Rev. Respir. Dis. 430–434 (1984). For example, heparinized (20 units/ml) peripheral venous blood was separated by Ficoll-Hypaque density gradient centrifugation to yield peripheral blood mononuclear cells (78 to 84% lymphocytes). A total of $10^5$ cells per well were suspended in RPMI 1640 medium (Flow Laboratories, Hamden, Conn.) supplemented with 2 mM glutamine (Sigma Chemical Co., St. Louis, Mo.), 100 U of penicillin and 100 μg of streptomycin (Sigma) per ml, and 10% heat-inactivated (56° C.), locally prepared, pooled human serum. Quadruplicate parallel cultures with or without WI-1 antigen were 18 hours prior to harvest, a pulse of 0.5 μCi of [$^3$H]-thymidine (specific activity, 6.7 Ci/mmol) (New England Nuclear, Boston, Mass.) was added. Cultures were terminated with a semi-automated harvester (M24v; Brandel, Rockville, Md.) onto a fiber glass filter. Radioactivity was assessed by liquid scintillation counting, with results expressed as either the change in disintegrations per minute of experimental minus the unstimulated control, or the ratio of experimental divided by control (stimulation index). A positive assay was defined as experimental minus control value greater than 2,000 and stimulation index greater than 5, and a borderline assay, as a value greater than 2,000 but stimulation index less than or equal to 5.

WI-1 was prepared as previously described. It was used at a final protein concentration of 0.6 μg/ml in the assay. The example assay demonstrated that a patient with blastomycosis responded to WI-1 and an individual with previous histoplasmosis had no response to WI-1.

Vaccine

Rabbit antiserum was produced in a New Zealand white rabbit immunized with 5-μg doses of WI-1 in 0.5 ml sterile deionized, distilled water (a typical liquid carrier). Also, some subcutaneous injections were given weekly for 4 weeks in 0.5 ml complete Freund adjuvant, and then biweekly in 0.5 ml incomplete Freund adjuvant. It will be appreciated that the ability of the antigen to readily raise an immune response is an important factor in providing a vaccine to inhibit growth of the yeast.

Discussion

We have located and isolated a protein, WI-1, that is abundantly expressed on *B. dermatitidis* yeasts. It was uniformly found in the five ATCC strains tested and it comprised 5% of the protein in the freeze extract we obtained after freezing and thawing the yeasts. Our tests indicate that the antigen is a protein and it contains little if any carbohydrate. Although its molecular weight varies slightly between strains, its size is approximately 120 kD. To reproducibly obtain material that will contain WI-1, rapid dialysis and lyophilization of a freeze extract is the method of choice. Concentrating the freeze extract by using a YM 100 filter prior to dialysis was associated with recovery of WI-1 of a lower molecular weight in the material obtained. The reason for this was not yet clear, but some degradation of the WI-1 molecule during the filtration procedure is a likely explanation. It is expected that the gene that expresses this material will at some point be located, cloned, and expressed using conventional techniques, thus providing an alternative to the freezing step.

WI-1 is a highly immunoreactive molecule and can be used to reliably detect antibody in infected patients. Western blots initially demonstrated that WI-1 was strongly recognized by sera of patients with blastomycosis, but not of patients with histoplasmosis or of healthy persons. Furthermore, using a 5 ng target of purified WI-1 labelled with $^{125}$I, we were able to detect antibody in 85% of the infected patients, and seropositive persons had a GMT of nearly 3,000. Ten patients with blastomycosis had no detectable antibody to WI-1. Possible explanations for these results include: isolated cutaneous disease (three patients); testing several months after treatment was completed (two); and testing on presentation with overwhelming pulmonary infection and adult respiratory distress syndrome (two). No reason was evident for the negative results in the remaining three patients, who had acute pulmonary disease.

The RIA we describe offers a significant advance for serological studies of blastomycosis. When results of the RIA for detection of antibody to WI-1 are compared to those reported using an enzyme immunoassay for detection of antibody to "A" antigen, several observations can be made: 1) antibody to WI-1 can be detected earlier, occasionally even at the onset of acute pulmonary illness; 2) antibody titers to WI-1 are far higher—the GMT is approximately 2.5 logs greater; and 3) antibody to WI-1 persists for a longer interval, although antibody to both antigens declines to low or undetectable levels by six months after illness onset in patients with resolution or successful treatment of disease. Despite the high sensitivity of the RIA, specificity was not a significant problem. Two patients with serologically confirmed histoplasmosis did have antibody titers to WI-1 just above the positive cutoff value of 1:40. However, increasing the cutoff value to 1:100 completely discriminated patients with blastomycosis from those with histoplasmosis without reducing the sensitivity or predictive values of the assay.

The lymphocyte assay provided an important tool to locate patients with remote infection. In remote infection cases, antibody titer may be small, thus frustrating the use of the RIA alone.

WI-1 appears to be a novel surface protein that is uniquely expressed on *B. dermatitidis* yeasts. SDS-PAGE showed no resemblance between WI-1 and components in the A-antigen or B-ASWS. Approximately $4.7\times10^6$ WI-1 molecules are presented on *B. dermatitidis* yeast, whereas no WI-1 could be detected on either *H. capsulatum* or *C. albicans* yeasts. In addition, no significant cross reactivity to WI-1 was found in patients with histoplasmosis, coccidioidomycosis, sporotrichosis, or candidiasis tested by immunoblotting and RIA.

The assay has wide applicability to many types of uses, but finds its greatest use in testing human and canine serum (e.g. blood, plasma, saliva). The assay is preferably an RIA, but it will be appreciated that other labelling (color, fluorescent, magnetic) can be used. Also, other forms of RIA can be used (e.g. iodine is not the only radioactive label). Moreover, while the entire WI-1 antigen is the preferred form, portions of it, extensions of it, or slight variations of it (all collectively "WI-1 proteinaceous material") may also be recognized by serum antibody. Further, the vaccine may also prove effective with both liquid and solid form carriers.

It will also be appreciated that using what have now become standard techniques, hybridomas and monoclonal antibodies can be developed for WI-1. These antibodies can in turn be used to test for and/or study this yeast.

It will be appreciated that the above describes only the preferred embodiments of the invention. A number of other modifications and changes are within the scope of the invention and are intended to be included within the scope of the claims The claims should be looked to in judging the scope of the invention.

We claim:

1. WI-1 proteinaceous material which has been obtained from *Blastomyces dermatitidis* by freezing the yeast, wherein the material is essentially free of other *B. dermatitidis*-derived cell wall proteinaceous material that has a size outside a 110 kD–125 kD size range.

2. Proteinaceous material that contains WI-1 and is essentially free of other *B. dermatitidis*-derived cell wall proteinaceous material that has a size outside a 110 kD–125 kD size range.

3. A composition for raising an immune response in an animal, comprising:

(a) proteinaceous material that contains WI-1 and is essentially free of other *B. dermatitidis*-derived cell wall proteinaceous material that has a size outside a 110 kD–125 kD size range; and (b) a suitable carrier.

4. The composition of claim 3, wherein the carrier is a liquid.

* * * * *